United States Patent [19]

Hlavka et al.

[11] Patent Number: 4,703,115

[45] Date of Patent: * Oct. 27, 1987

[54] PLATINUM COMPLEXES OF DIAMINO-DIDEOXY SUGARS AND DI- OR TRICARBOXYLIC ACIDS

[75] Inventors: Joseph J. Hlavka, Tuxedo; Ralph G. Child, Pearl River; Panayota Bitha, Pomona; Yang-i Lin, Nanuet, all of N.Y.

[73] Assignee: American Cyanamid Company, Stamford, Conn.

[*] Notice: The portion of the term of this patent subsequent to May 6, 2003 has been disclaimed.

[21] Appl. No.: 682,884

[22] Filed: Dec. 17, 1984

[51] Int. Cl.$^4$ .................. C07H 17/00; C07F 15/00
[52] U.S. Cl. .................... 536/55; 536/18.7; 536/22; 536/121; 556/137

[58] Field of Search .............. 514/23; 556/137; 536/121, 55, 18.7, 22

[56] References Cited

U.S. PATENT DOCUMENTS

| | | | |
|---|---|---|---|
| 3,074,927 | 4/1960 | Saltman et al. | 536/121 |
| 4,551,524 | 11/1985 | Kidani et al. | 536/121 |
| 4,587,331 | 5/1986 | Hlavka et al. | 536/55 |

*Primary Examiner*—Johnnie R. Brown
*Assistant Examiner*—Elli Peselev
*Attorney, Agent, or Firm*—Edward A. Conroy, Jr.

[57] ABSTRACT

Platinum complexes and Di- or Tricarboxylic acids which is then reacted with the appropriate di- or tricarboxylic acid in aqueous medium.

8 Claims, No Drawings

PLATINUM COMPLEXES OF DIAMINO-DIDEOXY SUGARS AND DI- OR TRICARBOXYLIC ACIDS

This invention is concerned with new compounds of the formula:

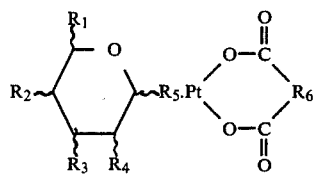

where $R_1$ is selected from the group consisting essentially of hydrogen, alkyl($C_1$-$C_3$), hydroxymethyl and aminomethyl; $R_2$, $R_3$, $R_4$ and $R_5$ are selected from the group consisting of hydroxy and amino, with the proviso that at least two of $R_2$, $R_3$, $R_4$, and $R_5$ must be hydroxy; and $R_6$ is selected from the group consisting essentially of

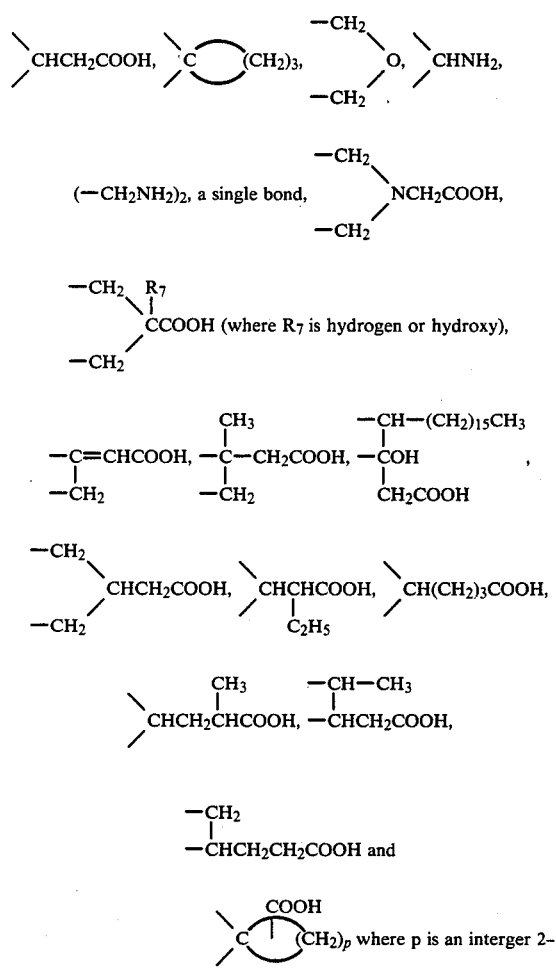

where p is an interger 2-5.

In addition this invention is concerned with the compound 2-deoxy-D-streptamine when coupled with any of the di- or tricarboxylic acids represented by the

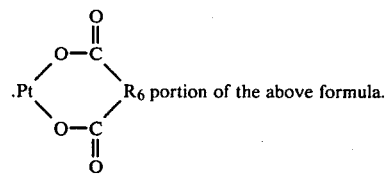

portion of the above formula.

DETAILED DESCRIPTION OF THE INVENTION

In general, the compounds of this invention may be prepared by reacting a 2,3-diamino-2,3-dideoxy sugar with potassium tetrachloroplatinate in aqueous medium, giving the platinum chloride-sugar complex, which is then reacted with the appropriate di- or tricarboxylic acid in aqueous medium.

The novel complexed compounds of this invention possess the property of inhibiting the growth of transplanted tumors in mammals as established by the following tests.

Lymphocytic Leukemia P388 Test

The animals used were BDF/1 mice, all of one sex, weighing a minimum of 18 g and all within a 3 g weight range. There were 5 or 6 animals per test group. The tumor transplant was by intraperitoneal injection of 0.5 ml of dilute ascitic fluid containing $10^6$ cells of lymphocytic leukemia P388. The test compounds were administered intraperitoneally on days 1, 5 and 9 relative to tumor inoculation, at various doses. The animals were weighed and the survivors recorded on a regular basis for 30 days. The median survival time and the ratio of survival time for treated (T)/control (C) animals were calculated. The positive control compound was Cisplatin. The results of this test with representative compounds of this invention appear in Table I.

TABLE I

Lymphocytic Leukemia P388 Test

| Compound | Dose (mg/kg) | Median Survival (Days) | T/C × 100 (%) |
|---|---|---|---|
| 2,3-diamino-2,3-dideoxy-D-glucopyranose compound with [1,1,2-ethanetricarboxylato-(2-)-$0^1,0^1$]platinum (1:1) | 100 | 14 | 131 |
| | 50 | 13.5 | 126 |
| | 25 | 12 | 112 |
| | 12.5 | 12 | 112 |
| Control | — | 10.7 | — |
| Cisplatin | 0.25 | 18 | 168 |
| | 0.06 | 15 | 140 |
| 2,3-diamino-2,3-dideoxy-D-galactopyranose compound with [[2,2'-oxybis[acetato](2-)-$0^1,0^1$]platinum (1:1) | 50 | 22 | 182 |
| | 25 | 19 | 157 |
| | 12 | 13.5 | 112 |
| | 6 | 16 | 132 |
| Control | — | 12.1 | — |
| Cisplatin | 1 | 21 | 174 |
| | 0.25 | 18 | 149 |
| | 0.06 | 13.5 | 112 |
| 2,3-diamino-2,3-dideoxy-D-galactopyranose compound with [1,1-cyclobutanedicarboxylato-(2-)-0,$0^1$]platinum | 100 | 20.5 | 192 |
| | 50 | 19 | 178 |
| | 25 | 15.5 | 145 |
| | 12.5 | 15 | 140 |
| Control | — | 10.7 | — |
| Cisplatin | 1 | 27.5 | 257 |
| | 0.25 | 18 | 168 |
| | 0.06 | 15 | 140 |
| (2-deoxy-D-streptamine)[2,2'-oxybis[acetato](2-)-$0^1,0^1$]-platinum | 50 | 14 | 130 |
| | 25 | 12.5 | 116 |
| | 12.5 | 12.5 | 116 |
| Control | — | 10.8 | — |
| Cisplatin | 1 | 26 | 241 |
| | 0.25 | 18 | 167 |
| | 0.06 | 12 | 111 |

TABLE I-continued

| | Lymphocytic Leukemia P388 Test | | |
|---|---|---|---|
| Compound | Dose (mg/kg) | Median Survival (Days) | T/C × 100 (%) |
| 2,3-diamino-2,3-dideoxy-D-glucopyranose compound with [ethanedioato(2-)-0¹,0²]-platinum (1:1) | 12.5 | 17 | 156 |
| | 6.2 | 14.5 | 133 |
| | 3.1 | 12.5 | 115 |
| Control | — | 10.9 | — |
| Cisplatin | 1 | 20.5 | 188 |
| | 0.25 | 15 | 138 |
| | 0.06 | 11.5 | 106 |
| (2-deoxy-D-streptamine)[1,1,2-ethanetricarboxylato(2-)-0¹,0¹]platinum | 100 | 13 | 119 |
| | 50 | 12 | 110 |
| | 25 | 12.5 | 115 |
| Control | — | 10.9 | — |
| Cisplatin | 1 | 20.5 | 188 |
| | 0.25 | 15 | 138 |
| | 0.06 | 11.5 | 106 |
| (2,3-diamino-2,3-dideoxy-D-glucopyranose)bis(glycinato-0)platinum (1:1) | 50 | 11.5 | 113 |
| | 25 | 11.5 | 113 |
| | 12.5 | 11 | 108 |
| | 6.2 | 10.5 | 103 |
| | 3.1 | 11 | 108 |
| Control | — | 10.2 | — |
| Cisplatin | 0.06 | 13 | 127 |

This aspect of the invention includes novel compositions of matter and the method of inducing the regression and/or palliation of leukemia and related cancers in mammals using the novel compounds of this invention when administered in amounts ranging from about 1 mg to about 1.2 g per square meter of body surface area per day. The interrelationship of dosages for animals of various sizes and species and humans (based on mg/m² of surface area) is described by Freireich, E. J., et al., Quantitative Comparison of Toxicity of Anticancer Agents in Mouse, Rat, Hamster, Dog, Monkey and Man. Cancer Chemother. Rep., 50, No. 4, 219-244, May 1966. A preferred dosage regimen for optimum results would be from about 3 mg/m²/day to about 200 mg/m²/day, and such dosage units are employed that a total of from about 5 mg to about 360 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular or subcutaneous routes.

The active compounds may be administered parenterally. Solutions or dispersions of the active compound can be prepared in water, suitably mixed with a surfactant such as hydroxypropylcellulose. Dispersions can also be prepared in glycerol, liquid polyethylene glycols, and mixtures thereof in oils. Under ordinary conditions of storage and use these preparations contains a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol, liquid polyethylene glycol), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be obtained by the use in the compositions of agents which delay absorption, for example, aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subject to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of adminitration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the host harboring the cancer. As used herein, cancer disease means blood malignancies such as leukemia, as well as other solid and nonsolid malignancies such as the melanocarcinomas, lung carcinomas and mammary tumors. By regression and palliation is meant arresting or retarding the growth of the tumor or other manifestation of the disease compared to the course of the disease in the absence of treatment.

This invention will be described in greater detail in conjunction with the following non-limiting specific examples.

EXAMPLE 1

2,3-Diamino-2,3-dideoxy-D-glucopyranose compound with [1,1,2-ethanetricarboxylato(2-)-$O^1,O^1$]platinum A solution of 1.97 g of 2,3-diamino-2,3-dideoxy-D-glucose dihydrochloride in 60 ml of water was adjusted to pH 7.5 and then filtered. The filtrate was added to a solution of 3.25 g of potassium tetrachloroplatinate in 50 ml of water, stirred for 24 hours, evaporated in vacuo to 20 ml and then cooled in an ice bath. The resulting precipitate was collected, giving 1.4 g of 2,3-diamino-2,3-dideoxy-D-glucopyranose compound with platinum chloride (1:1).

To a solution of 500 mg of 2,3-diamino-2,3-dideoxy-D-glucopyranose compound with platinum chloride (1:1) in 75 ml of water was added 425 mg of 1,1,2-ethanetricarboxylic acid. The mixture was stirred 24 hours and then the solid was collected, giving 350 mg of the desired product.

EXAMPLE 2

2,3-Diamino-2,3-dideoxy-D-galactopyranose compound with [2,2'-oxybis[acetato](2-)-$O^1,O^1$]platinum 2,3-Diamino-2,3-dideoxy-D-galactose was reacted with potassium tetrachloroplatinate as described in Example 1, giving the platinum chloride complex.

To a solution of 528 mg of this complex in 75 ml of water was added 414 mg of the disilver salt of diglycolic acid. This reaction mixture was stirred overnight and the resulting precipitate collected, giving 400 mg of the desired product.

EXAMPLE 3

2,3-Diamino-2,3-dideoxy-D-galactopyranose, compound with [1,1-cyclobutanedicarboxylato-(2-)-O,$O^1$]platinum (1:1)

To a solution of 500 mg of 2,3-diamino-2,3-dideoxy-D-galactopyranose, compound with platinum dichloride in 75 ml of water was added 405 mg of the disilver salt of 1,1-cyclobutanedicarboxylic acid. The mixture was stirred overnight, then filtered and the filtrate evaporated to dryness, giving the desired product.

EXAMPLE 4

(2-Deoxy-D-streptamine)[2,2'-oxybis-[acetato](2-)-$O^1,O^1$]platinum

To a suspension of 500 mg of 2-deoxy-D-streptaminie platinum dichloride in 250 ml of water was added 403 mg of the disilver salt of diglycolic acid. The mixture was stirred overnight, then filtered and the filtrate evaporated to dryness giving 250 mg of the desired product.

EXAMPLE 5

2,3-Diamino-2,3-dideoxy-D-glucopyranose, compound with [ethanediato(2-)-$O^1,O^2$]platinum (1:1)

To a solution of 529 mg of 2,3-diamino-2,3-dideoxy-D-glucopyranose platinum dichloride salt in 75 ml of water was added 361 mg of the disilver salt of oxalic acid. The mixture was stirred overnight, then filtered and the filtrate evaporated to dryness in vacuo, giving 420 mg of the desired product.

EXAMPLE 6

(2-Deoxy-D-streptamine)[1,1,2-ethanetricarboxylato(2-)-$O^1,O^1$]platinum

To 600 mg of 2-deoxy-D-streptamine platinum dichloride salt in 350 ml of water was added 526 mg of the disilver salt of 1,1,2-ethanetricarboxylic acid. The mixture was stirred overnight, then filtered and the filtrate evaporated, giving 280 mg of the desired product.

EXAMPLE 7

(2,3-Diamino-2,3-dideoxy-D-glucopyranose)-bis(-glycinato-O)platinum

To a solution of 516 mg of 2,3-diamino-2,3-dideoxy-D-glucopyranose platinum dichloride salt in 75 ml of water was added 422 mg of the silver salt of glycine. The mixture was stirred overnight, then filtered and the filtrate evaporated to dryness, giving 380 mg of the desired product.

We claim:

1. A compound of the formula:

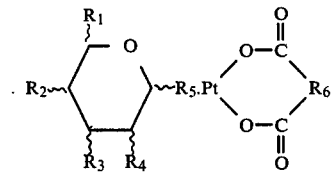

wherein $R_1$ is hydrogen, alkyl($C_1$–$C_3$), hydroxymethyl or aminomethyl; $R_2$, $R_3$, $R_4$ and $R_5$ are each hydroxy or amino with the proviso that at least two of $R_2$, $R_3$, $R_4$ and $R_5$ must be hydroxy; and $R_6$ is selected from the group consisting of moieties of the formulae:

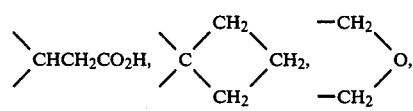

-continued

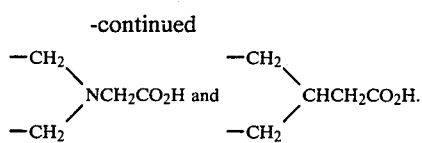

2. The compound according to claim 1; 2,3-diamino-2,3-dideoxy-D-glucopyranose compound with [1,1,2-ethanetricarboxylato(2-)-O$^1$,O$^1$]platinum.

3. The compound according to claim 1; 2,3-diamino-2,3-dideoxy-D-galactopyranose compound with [2,2'-oxybis[acetato](2-)-O$^1$,O$^1$]platinum.

4. The compound according to claim 1; 2,3-diamino-2,3-dideoxy-D-galactopyranose compound with [1,1-cyclobutanedicarboxylato(2-)-O,O$^1$]platinum(1:1).

5. The compound according to claim 1; 2,3-diamino-2,3-dideoxy-D-glucopyranose compound with [ethanedioato(2-)-O$^1$,O$^2$]platinum (1:1).

6. The compound according to claim 1; (2,3-diamino-2,3-dideoxy-D-glucopyranose)bis(glycinato-O)platinum.

7. The compound (2-deoxy-D-streptamine)[2,2'-oxybis[acetato](2-)-O$^1$,O$^1$]platinum.

8. The compound (2-deoxy-D-streptamine)[1,1,2-ethanetricarboxylato(2-)-O$^1$,O$^1$]platinum.

* * * * *